United States Patent [19]

Task et al.

[11] Patent Number: 4,687,338
[45] Date of Patent: Aug. 18, 1987

[54] METHOD OF MEASUREMENT OF HAZE IN TRANSPARENCIES

[75] Inventors: Harry L. Task, Dayton; Louis V. Genco, Enon, both of Ohio

[73] Assignee: The United States of America as represented by the Secretary of the Air Force, Washington, D.C.

[21] Appl. No.: 463,191

[22] Filed: Feb. 2, 1983

[51] Int. Cl.$^4$ ............................................. G01N 21/47
[52] U.S. Cl. ..................................... 356/446; 356/237
[58] Field of Search ............... 356/337, 338, 340, 342, 356/445, 446, 447, 448, 215, 221, 236, 237; 250/562, 572

[56] References Cited

U.S. PATENT DOCUMENTS

| | | | |
|---|---|---|---|
| 1,949,619 | 3/1934 | Pfund | 356/446 |
| 2,254,062 | 8/1941 | Devol | 356/446 |
| 2,604,809 | 7/1952 | Mitchell | 88/14 |
| 2,986,065 | 5/1961 | Newman | 355/446 |
| 3,222,978 | 12/1965 | Dreyfus | 88/14 |
| 3,782,836 | 1/1974 | Fey et al. | 355/446 |
| 3,804,521 | 4/1974 | Sprague | 356/109 |
| 4,373,818 | 2/1983 | Yamamoto et al. | 356/445 |

*Primary Examiner*—Bruce Y. Arnold
*Attorney, Agent, or Firm*—Fredric L. Sinder; Donald J. Singer; John R. Flanagan

[57] ABSTRACT

A method of measuring haze of an aircraft transparency includes producing a first reading representative of the level of light scattered by an area of a transparency under test while on the aircraft when it is illuminated by a known light source, and producing a second reading representative of the level of light scattered by a predetermined, preferably worst haze condition, reference plate when it is illuminated by the light source in place of the transparency. Then, a ratio of the first and second readings is calculated to provide a quantitative measure proportional to the degree of haze in the transparency test area.

10 Claims, 2 Drawing Figures

METHOD OF MEASUREMENT OF HAZE IN TRANSPARENCIES

RIGHTS OF THE GOVERNMENT

The invention described herein may be manufactured and used by or for the Government of the United States for all governmental purposes without the payment of any royalty.

CROSS REFERENCE TO RELATED APPLICATIONS

Reference is hereby made to the following co-pending U.S. application disclosing subject matter which is related to the present invention: "Transparency Halation Measurement," by Louis V. Genco et al, U.S. Pat. Ser. No. 251,823, filed Apr. 7, 1981 now U.S. Pat. No. 4,397,554.

BACKGROUND OF THE INVENTION

1. Field of the Invention

The present invention broadly relates to measuring halation in transparencies, such as aircraft windscreens made of plastic or the like, and, more particularly, is concerned with a method of providing a quantitative measure proportional to the degree of haze or transparency quality degradation.

2. Description of the Prior Art

The requirement for effective birdstrike protection in today's high-performance aircraft has caused a transition from glass canopies and windscreens to laminated or monolithic plastic transparencies. Plastic aircraft transparencies have a life cycle which appears to be limited by the surface qualities of the transparency. Since the hardness of the plastic surface is less than that of glass, the plastic transparencies are much more susceptible to environmental surface damage than the glass transparencies which they replace.

One of the most significant optical changes that occurs during the life cycle of the plastic transparency is an increase in haze or halation in the transparency. As halation increases, light appears to "spread" from its source, causing a disabling glare or significant reduction in contrast of objects seen through the transparency. This disabling glare can lead to flight safety problems as the pilot's view of the external world is restricted.

Halation, the spreading of light beyond its proper boundaries due to internal reflections or light scattering, is evident whenever a bright light source appears in the field of view of the pilot. One source of halation is particles included in the transparency. Another source of halation is the "volume haze" inherent in most aircraft transparencies. A third, and probably most significant, source of halation is the accumulation of scratches on the surfaces of the transparencies. The effect of aging on a transparency is to increase this source of halation. These scratches tend to cause light to be more evenly distributed over the surface of the transparency, resulting in disabling glare or reduction of contrast between a target and its background.

One recent method of measuring haze disclosed in the above cross-referenced patent application uses an intense light source placed on one side of the transparency to be tested, and a camera and annular neutral density filter positioned on the opposite side. The filter is aligned between the light source and camera lens so as to occlude or shade the lens from the direct light rays, whereas light scattered by portions of the transparency outside the periphery of the filter may be recorded on photographic film in the camera. The annular filter contains contrasting rings of varying shades of gray which facilitate standardization of halation measurements made on different transparencies or the same transparency at different periods in its life cycle.

While the above-referenced method has proven to be satisfactory, it does require that equipment be positioned on both sides of the transparency and accurate alignment achieved between the components thereof. Consequently, a need exists for a halation measuring system which is easier to set up for use.

SUMMARY OF THE INVENTION

The present invention provides a haze measurement method designed to substantially satisfy the aforementioned need. The invention is capable of measuring the light scattering effects, or haze, in transparencies from one side thereof. Furthermore, in contrast to the qualitative measurement of halation provided by the method of the above-referenced application, the method of the present invention provides a quantitative measure in the form of a value which is proportional to the degree of haze.

Accordingly, the present invention broadly provides a method of measuring haze in a transparency which basically includes the steps of: (a) producing a first reading representative of the level of light scattered by an area of a transparency under test when illuminated by a known light source; (b) producing a second reading representative of the level of light scattered by a predetermined haze reference plate when illuminated by the known light source; and (c) calculating a ratio of the first and second readings to provide a quantitative measure proportional to the degree of haze in the transparency test area. Preferably, the predetermined haze reference plate simulates a worst possible haze condition. A further refinement of the above-defined basic haze measuring method includes the additional step of producing a third reading representative of the level of light scattered by the transparency test area when the known light source is turned off, and modification of step (c) above to calculating a quantitative measure of the degree of haze in the transparency test area by dividing the second reading into the difference between the first and third readings.

DETAILED DESCRIPTION OF THE INVENTION

Figure 1:
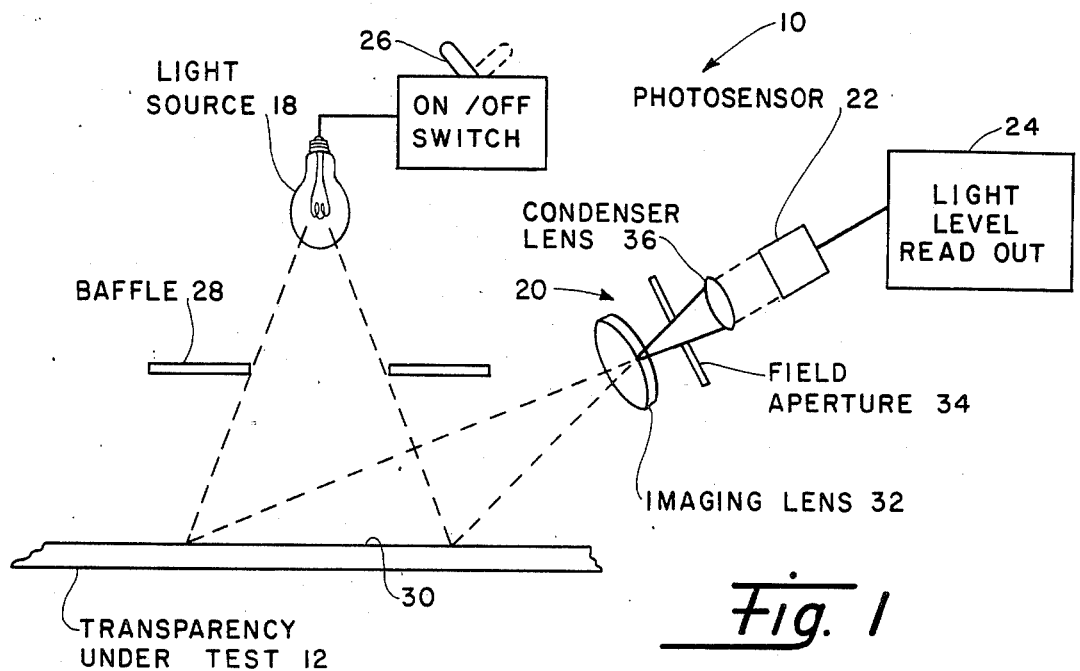
FIG. 1 is a side elevational view in schematical form of the system for carrying out the haze measuring method of the present invention on a transparency.

Referring now to the drawings, and more particularly to FIG. 1, there is shown the preferred embodiment of the haze measuring system for carrying out the method of the present invention, being generally designated 10. The measuring system 10 is designed for producing readings representative of the level of light scattered by a test area of a transparency 12 and by a haze reference plate 16 (FIG 2) to facilitate calculation of a haze index for the transparency test area 12.

The measuring system 10 includes the haze reference plate 16, a light source 18, a relay lens arrangement 20, a photosensor 22 and a light level read out device 24. With the exception of the haze reference plate 16, all the above-mentioned parts of the system 10 are conventional, commerically-available components. The light source 18, relay lens arrangement 20 and photosensor 22 are all located on the same side of the transparency 12. The light source 18 may be actuated off or on by a suitable device, such as on/off switch 26. The light from the light source 18 may be noncoherent light emitted by an ordinary light bulb. A baffle 28 is positioned between source 18 and the transparency 12 under test, or the haze reference plate 16 when it replaces the transparency 12. The baffle 28 "shapes" the light from the light source 18 to illuminate a desired area 30 of the transparency 12 being tested. The relay lens arrangement 20 and photosensor 22 are positioned at a preselected angle from the transparency test area.

The system 10 makes use of the fact that when light is incident on a surface that has been randomly scratched or pitted, the light is scattered in all directions not just in the forward direction. Accordingly, the light which is scattered toward an imaging lens 32 is received and gathered by the lens 32 and then transmitted or relayed through a field aperture 34 to a condensor lens 36. The lenses 32, 36 and field aperture 34 make up the relay lens arrangement 20 which was briefly mentioned earlier.

From the condenser lens 36, the light is transmitted to the photometrically-calibrated light sensor 22, which is electrically connected to the light level read out device 24 from which a first reading, R, may be made representative of the level of light scattered by the tested area 30 of the transparency 12.

Figure 2:
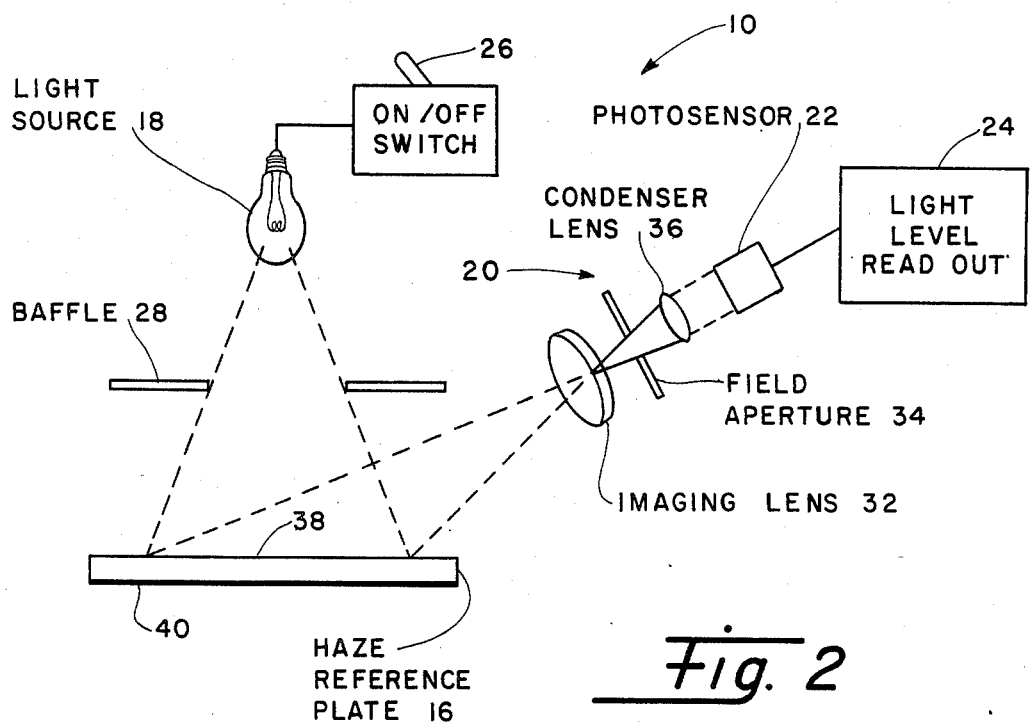
FIG. 2 is a side elevational view in schematical form of the system of FIG. 1 but now shown in conjunction with a haze reference plate instead of the transparency.

Taken alone, the first reading R would have little utility. It must be compared to something to give it meaning. In other words, to determine the severity of the scratch/pit degradation of the tested area 30 of the transparency 12 this first scattered light level reading R must be scaled by some reference reading. Therefore, a second reading, $R_r$, is made following the same procedures as before, but after inserting a predetermined haze reference plate 16 into the measurement area in place of the transparency 12, such as is seen in FIG. 2. Preferably, the haze reference plate 16 is made of transparent material and has a maximally scratched and pitted surface 38 to simulate the worst possible haze condition. The plate 16 is so positioned in the test area that the surface 38 is on the side of the plate facing the light source 18. On the opposite side of the plate 16 is provided an opaque black backing 40 for preventing the transmission of any light from the opposite side of the plate 16. This will augment the maximum back scattering of light from the plate 16 at the one side facing the light source 18 and the imaging lens 32.

Thus, the second reading $R_r$ represents the level of light scattered by the predetermined haze reference plate 16 when illuminated by the known light source 18, while the first reading R represents the level of light scattered by the test area of the transparency 12 when illuminated by the known light source 18. By calculating the ratio of these readings, $R/R_r$, a quantitative measure proportional to the degree of haze in the transparency test area 30 is provided.

The above-described haze measuring method is preferably carried out in a dark environment. Further, the light source 18 would be isolated from the relay lens arrangement 20 and photosensor 22 by a suitable enclosure (not shown) so as to avoid the projection of unwanted light to the arrangement 20 and photosensor 22.

While the measurement of the predetermined haze reference plate 16 should always be made in a dark environment, in most instances some extraneous ambient light will be present in the actual test environment. In those circumstances, a third, baseline reading, $R_o$, is made in the presence of the transparency 12, but with the light source 18 turned off as would be in the case when switch 26 is disposed in its broken line position shown in FIG. 1. The third reading $R_o$, therefore, represents the level of light scattered by the transparency test area 30 when the known light source is turned off. A haze index, H, being a more refined quantitative measure of the degree of haze in the transparency test area, may be calculated by dividing the second reading into the difference between the first and third reading as follows:

$$H = \frac{R - R_o}{R_r}$$

where:
H = haze index (between 0 to 1),
R = first reading taken from transparency with light on,
$R_r$ = second, reference reading taken from haze reference plate, and
$R_o$ = third, baseline reading taken from transparency with light off.

It is readily apparent that the system 10 may take the form of a portable device and is ideal for assessing transmission quality of plastic aircraft windscreens that degrade over time due to surface abrasions and crazing.

It is thought that the haze measuring method of the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

Having thus described the invention, what is claimed is:

1. A method of measuring haze of an aircraft transparency, comprising the steps of:
    a. illuminating a preselected test area of a surface of said aircraft transparency on the aircraft with a light source of known intensity and measuring the intensity of light back scattered from said test area to a preselected position to produce a first reading representative of the level of light scattered by said test area of said transparency;
    b. illuminating a standard surface area of size equal to said test area with said light source and measuring the intensity of light back scattered therefrom to said preselected position to produce a second reading representative of the level of light scattered by said standard surface; and
    c. calculating the ratio of said first reading to said second reading to define a quantitative measure characterizing the degree of haze of said transparency.

2. The haze measuring method as recited in claim 1, wherein said standard surface is randomly scratched to a predetermined surface condition to simulate a preselected standard haze producing condition.

3. The haze measuring method as recited in claim 1, wherein step a. thereof includes:
- illuminating said test area of said transparency at one side thereof using said known light source;
- receiving light scattered by said transparency test area at said one side thereof;
- sensing the received light; and
- making said first reading representative of the level of said sensed light.

4. The haze measuring method as recited in claim 3, wherein step b thereof includes:
- illuminating said standard surface area at one side thereof using said known light source;
- receiving light scattered by said standard surface area at said one side thereof;
- sensing the received light; and
- making said second reading representative of the level of said sensed light.

5. The haze measuring method as recited claim 4, wherein said standard surface is maximally scratched and pitted to simulate a haze condition of predetermined severity.

6. A method of measuring haze of an aircraft transparency, comprising the steps of:
 a. illuminating a preselected test area of a surface of said aircraft transparency on the aircraft with a light source of know intensity and measuring the intensity of light back scattered from said test area to a preselected position to produce a first reading representative of the level of light scattered by said test area of said transparency;
 b. illuminating a standard surface area of size equal to said test area with said light source in a dark environment from which all other light sources have been excluded and measuring the intensity of non-specular light back scattered therefrom to said preselected position to produce a second reading representative of the level of light scattered by said standard surface;
 c. measuring the intensity of light back scattered to said position from said transparency with said source turned off to produce a third reading representative of the level of extraneous light scattered by said transparency test area in producing said first reading; and
 d. calculating the ratio of the difference between said first and third readings to said second reading to define a quantative measure of the degree of haze in said transparency.

7. The haze measuring method as recited in claim 6, wherein said standard surface is randomly scratched to a predetermined surface condition to simulate a preselected standard haze producing condition.

8. A method of measuring haze of an aircraft transparency, comprising the steps of:
 a. illuminating a preselected test area of said aircraft transparency on the aircraft at one side of the transparency using a light source of known intensity;
 b. gathering light scattered by said test area of said transparency at one side thereof;
 c. sensing the level of said scattered light;
 d. making a first reading representative of the level of the sensed light scattered by said transparency test area at said one side thereof;
 e. repeating steps a. through c. utilizing a standard surface area in place of said transparency under test, wherein said standard surface is randomly scratched to a predetermined surface condition to simulate a preselected standard haze producing condition, the steps performed in a dark environment from which 11 light sources other than said light source have been excluded;
 f. making a second reading representative of the level of sensed light scattered by said standard surface areas at one side thereof;
 g. repeating steps b. and c. when said light source is turned off to sense ambient light;
 h. making a third reading representative of the level of sensed extraneous light scattered by said transparency test area; and
 i. calculating a haze index for said transparency by dividing said second reading into the difference between said first and second readings.

9. A method of measuring haze of an aircraft transparency, comprising the steps of:
 a. illuminating a preselected test area of a surface of said aircraft transparency on the aircraft with a light source of known intensity and measuring the intensity of light back scattered from said test area to a preselected position to produce a first reading representative of the level of light scattered by said test area of said transparency;
 b. illuminating a standard surface area of size equal to said test area with said light source and measuring the intensity of light back scattered therefrom to said preselected position to produce a second reading representative of the level of light scattered by said standard surface; and
 c. calculating the ratio of said first reading to said second reading to define a quantitative measure characterizing the degree of haze of said transparency.

10. A method of measuring haze of an aircraft transparency, comprising the steps of:
 a. illuminating a preselected test area of a surface of said aircraft transparency on the aricraft with a light source of known intensity and measuring the intensity of light back scattered from said test area to a preselected position to produce a first reading representative of the level of light scattered by said test area of said transparency;
 b. illuminating a standard surface area of size equal to said test area with said light source in a dark environment from which all other light sources have been exlcused and measuring the intensity of light back scattered therefrom to said preselected position to produce a second reading representative of the level of light scattered by said standard surface;
 c. measuring the intensity of non-specular light back scattered to said position from said transparency with said source turned off to produce a third reading representative of the level of extraneous light scattered by said transparency test area in producing said first reading; and
 d. calculating the ratio of the difference between said first and third readings to said second reading to define a quantitative measure of the degree of haze in said transparency.

* * * * *